(12) United States Patent
Qin et al.

(10) Patent No.: US 11,652,981 B2
(45) Date of Patent: May 16, 2023

(54) RESOLUTION TEST CHART AND ARTIFICIAL EYE FOR ASSESSING FUNDUS IMAGING SYSTEMS

(71) Applicant: NIKON CORPORATION, Tokyo (JP)

(72) Inventors: Wan Qin, Oro Valley, AZ (US); Brian Stamper, Tucson, AZ (US)

(73) Assignee: Nikon Corporation

( * ) Notice: Subject to any disclaimer, the term of this patent is extended or adjusted under 35 U.S.C. 154(b) by 0 days.

(21) Appl. No.: 16/808,300

(22) Filed: Mar. 3, 2020

(65) Prior Publication Data
US 2020/0288117 A1 Sep. 10, 2020

Related U.S. Application Data

(60) Provisional application No. 62/813,682, filed on Mar. 4, 2019.

(51) Int. Cl.
*H04N 17/00* (2006.01)
*A61B 3/00* (2006.01)
*G06V 40/18* (2022.01)

(52) U.S. Cl.
CPC ......... *H04N 17/002* (2013.01); *A61B 3/0025* (2013.01); *G06V 40/193* (2022.01)

(58) Field of Classification Search
CPC ...... H04N 17/002; A61B 3/0025; A61B 3/12; G06K 9/0061; G09B 23/30;
(Continued)

(56) References Cited

U.S. PATENT DOCUMENTS 8,699,015 B2    4/2014  Saito et al.
11,092,717 B2 * 8/2021  Capasso ................. G02B 1/002
(Continued)

FOREIGN PATENT DOCUMENTS

CN    203354522 U  * 12/2013
CN    203354522 U    12/2013
(Continued)

OTHER PUBLICATIONS

Retinal vessel model fabricated on a curved surface structure for a simulation of microcannulation (Year: 2016).*
(Continued)

*Primary Examiner* — Vu Le
*Assistant Examiner* — Winta Gebreslassie
(74) *Attorney, Agent, or Firm* — Roeder & Broder LLP; Steven G. Roeder

(57) ABSTRACT

An assessment assembly (10) for assessing a fundus imaging system (12) includes at least one, curved, flexible resolution test chart (40). Each of the resolution test charts (40) can include a chart body (342), and a plurality of spaced apart chart features (344). Moreover, each of the resolution test charts (40) can be fixedly coupled to an artificial retina region (36) of an artificial eye (14). The artificial retina region (36) can be shaped and sized similar to a retina region (19E) of a human eye (19), and the artificial retina region (36) can have scattering and depolarization properties that are similar to the scattering and depolarization properties of the retina region (19E) of the human eye (19). The fundus imaging system (12) can capture one or more images (20) of the resolution test charts (40) that are evaluated to determine a resolution of the fundus imaging system (12).

20 Claims, 7 Drawing Sheets

(58) Field of Classification Search
CPC ...... G02B 2027/0138; G02B 2027/014; G02B 27/0093; G02B 21/0032; G02B 27/62; G02B 7/021; G02B 7/003
See application file for complete search history.

(56) References Cited

U.S. PATENT DOCUMENTS

| | | | |
|---|---|---|---|
| 2006/0268224 A1* | 11/2006 | Brent | G02C 7/02 351/159.18 |
| 2017/0221203 A1* | 8/2017 | Iwase | G06V 10/60 |
| 2019/0159673 A1* | 5/2019 | Yates | A61B 3/14 |
| 2019/0278972 A1 | 9/2019 | Anderson et al. | |

FOREIGN PATENT DOCUMENTS

| | | | |
|---|---|---|---|
| JP | 2002165759 | | 6/2002 |
| JP | 2002-165759 A | | 11/2002 |
| JP | 2011235084 A | | 11/2011 |
| JP | 201976181 | | 5/2019 |
| JP | 2020121027 A | * | 8/2020 |
| JP | 2020121027 A | | 8/2020 |

OTHER PUBLICATIONS

"Retinal vessel model fabricated on a curved surface structure for a simulation of microcannulation" Takeshi Hayakawa, Ippei Kato, Fumihito Arai, Mamoru Mitsuishi, Naohiko Sugita, Kanako Harada, Shinichi Tanaka, Yasuo Noda & Takashi Ueta (Year: 2016).*

* cited by examiner

RESOLUTION TEST CHART AND ARTIFICIAL EYE FOR ASSESSING FUNDUS IMAGING SYSTEMS

RELATED APPLICATION

This application claims priority on U.S. Provisional Application No. 62/813,682 filed on Mar. 4, 2019, and entitled "RESOLUTION TEST CHART AND ARTIFICIAL EYE FOR ASSESSING FUNDUS IMAGING SYSTEMS". As far as permitted, the contents of U.S. Provisional Application No. 62/813,682 is incorporated herein by reference.

BACKGROUND

Fundus imaging systems are used to capture one or more images of an eye to evaluate the eye for diagnosing and treating patients in Ophthalmology. For example, the images can be used to diagnose retinal conditions such as Macular Degeneration and Diabetic Retinopathy. There is a never ending need to improve the quality of the fundus imaging system to provide improved images and improve the diagnoses and treating of patients.

SUMMARY

An assessment assembly for assessing a fundus imaging system includes at least one, curved, flexible, resolution test chart. In one embodiment, each of the resolution test charts includes a chart body and at least one chart feature. With this design, the resolution test chart can be coupled to a curved retina region of an artificial eye. Subsequently, the fundus imaging system can capture one or more images of the curved, resolution test charts. Next, the captured images can be evaluated with reference to the curved, resolution test charts to evaluate a resolution of the fundus imaging system. With this design, the problem of assessing the imaging resolution of the fundus imaging systems is solved by integrating special resolution test charts in the artificial retina and subsequently analyzing captured images of the resolution test charts.

In one embodiment, each of the resolution test charts is flexible. For example, each of the resolution test charts can have an elasticity of less than 1.2 mega pascal.

Moreover, each of the resolution test charts is relatively small. For example, each of the resolution test charts can have a chart surface area of less than fifty millimeters squared. As another example, each of the test charts can have a chart surface area of less than twenty-five millimeters squared.

Each of the resolution test charts can have a plurality of spaced apart chart features, with at least two of the chart features having a different feature width. In one embodiment, each chart feature is ring shaped. Further, the chart features can be substantially concentric.

Additionally, the assessment assembly can include an analysis system that analyzes information from at least one image captured of the resolution test chart by the fundus imaging system to assess a resolution of the fundus imaging system. With the present design, the analysis system can review one or more images and provide the resolution of the fundus imaging system at a plurality of spaced apart locations.

In another embodiment, the present invention is directed to a method for assessing a fundus imaging system. The method can include (i) providing an artificial eye that includes a curved (e.g. spherical) retina region; (ii) coupling at least one, curved, resolution test chart to the retina region, each of the test charts including at least one chart feature; and (iii) capturing at least one image of the curved retina region including at least one resolution test chart with the fundus imaging system. In this embodiment, the method can include reviewing the information from at least one image to assess the fundus imaging system.

In still another embodiment, the method for assessing a fundus imaging system can include (i) providing at least one, curved, resolution test chart, each of the resolution test charts including at least one chart feature; and (iii) capturing at least one image of the at least one resolution test chart with the fundus imaging system.

In another embodiment, an artificial eye that mimics a human eye, includes a curved, artificial retina region that is shaped and sized similar to the human eye. Further, the artificial retina region has scattering and depolarization properties that are similar to the scattering and depolarization properties of the human eye.

In alternative, non-exclusive embodiments, the curved retina region has a degradation in degree of polarization that is within 100, 99, 95, 90, 85, 80, 75, 70, 65 or 60 percent of a degradation in degree of polarization of a retina of the human eye. For example, the curved retina region can be made of a polydimethylsiloxane and titanium dioxide mixture.

Moreover, one or more, curved, flexible, resolution test charts can be secured to the curved retina region, wherein each of the at least one resolution test charts includes a chart body and at least one chart feature.

In another embodiment, the present invention is directed to a method for making an artificial eye.

In one implementation, at least one of the resolution test charts is coupled to an ultra-widefield region of the artificial eye.

DETAILED DESCRIPTION

Figure 1:
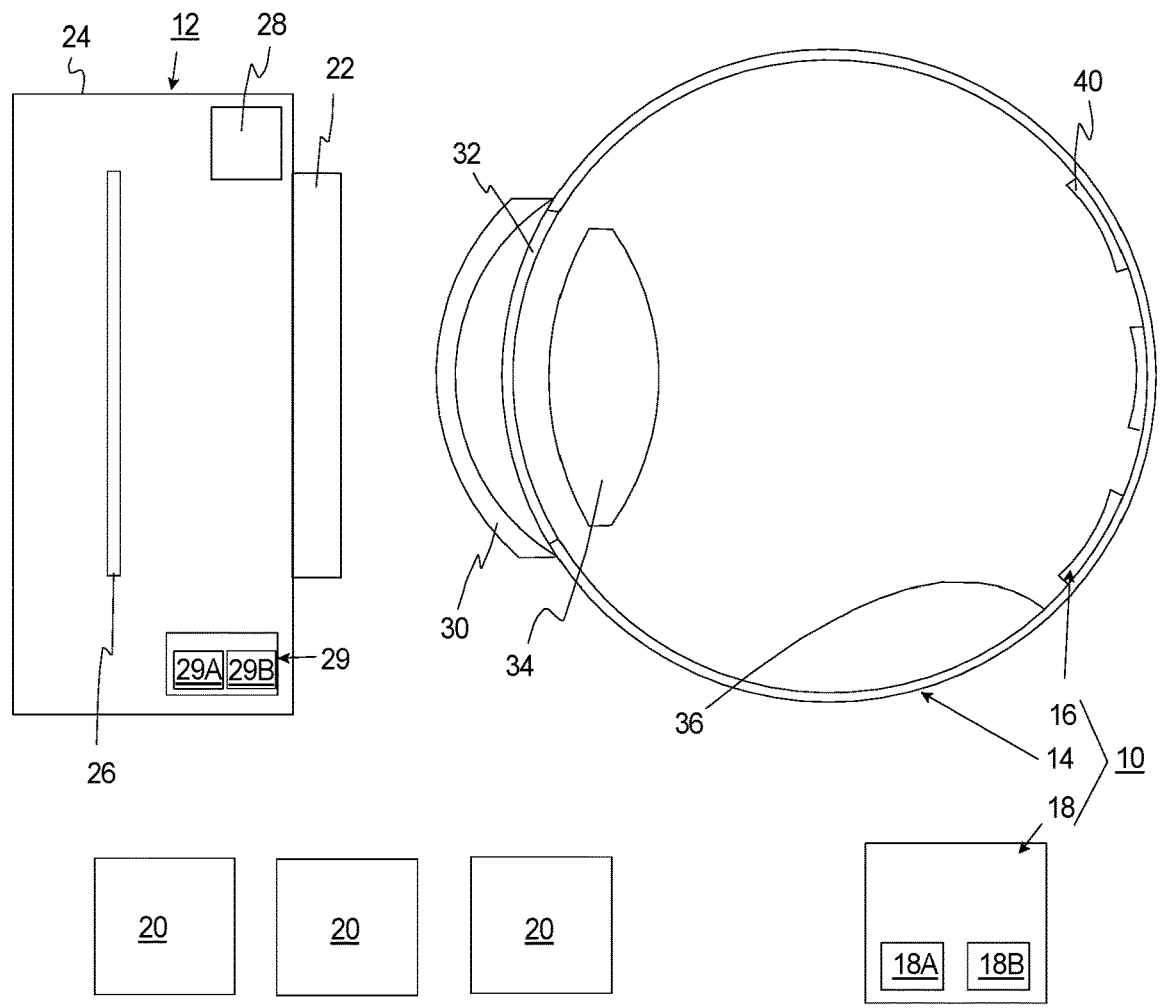
FIG. 1 is a simplified illustration of a human eye, a fundus imaging system and an assessment assembly having features of the present invention.
Figure 1:
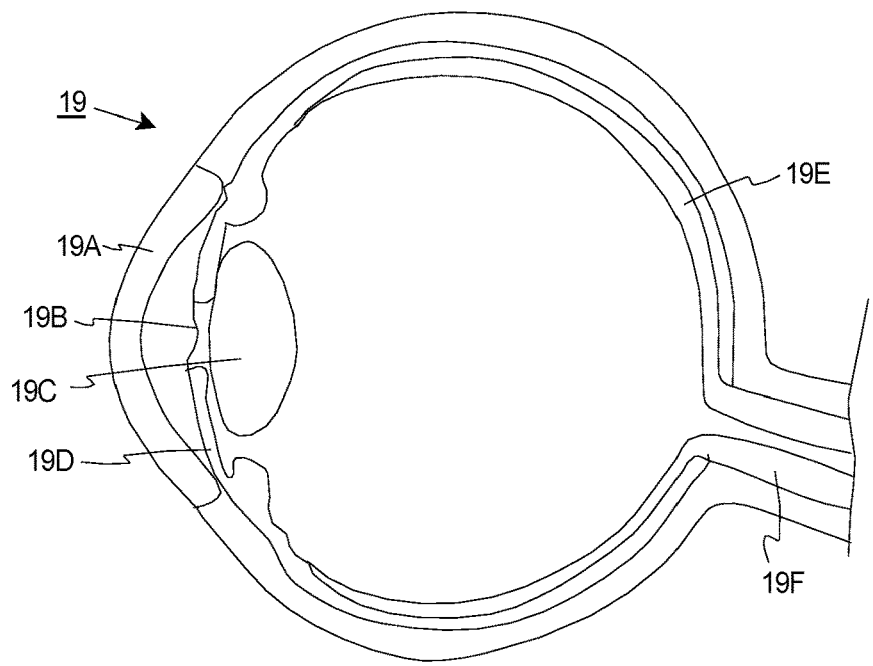

The present invention is directed to an assessment assembly 10 for assessing a fundus imaging system 12 having a curved imaging field. In the simplified embodiment illustrated in FIG. 1, the assessment assembly 10 includes an artificial eye 14, a resolution chart assembly 16 fixedly coupled to the artificial eye 14, and an analysis system 18. The design of the components of the assessment assembly 10 can be varied pursuant to the teachings provided herein.

As non-exclusive examples, the assessment assembly 10 can be used to (i) initially design test fundus imaging systems 12, (ii) optimize signal to noise in existing fundus imaging systems 12, (iii) perform routine quality control in existing fundus imaging systems 12, and/or (iv) compare performance between fundus imaging systems 12.

FIG. 1 also includes a simplified illustration of a human eye 19 that includes a cornea 19A, a pupil 19B, a lens 19C, an iris 19D, a retina 19E, and an optic nerve 19F that are labeled.

It should be noted that in the simplified schematic of FIG. 1, the fundus imaging system 12 is approximately the same size as the artificial eye 14. Typically, however, the fundus imaging system 12 will be larger than the artificial eye 14 and/or the human eye 19 of the patient.

With the present design, the fundus imaging system 12 can be controlled to capture one or more images 20 (three are illustrated as boxes in FIG. 1) of the artificial eye 14 and the resolution chart assembly 16. Subsequently, information from one or more of the images 20 can be analyzed (e.g. by the analysis system 18) to evaluate the optical resolution of the fundus imaging system 12 at a number of spaced apart field locations in the field of view of the fundus imaging system 12. For example, the analysis system 18 can provide a quantitative measurement of the resolution of the fundus imaging system 12 (i) at a center of the field of view ("central part"), (ii) at the periphery of the field of view ("peripheral part"), (iii) at an ultra-widefield portion; and/or (iv) at a number of spaced apart locations between the center and the periphery.

Optical resolution is a key characteristic of the fundus imaging system 12 as it describes the ability of the fundus imaging system 12 to resolve detail in the object (e.g. the patient's eye 19) being imaged. Thus, the assessment assembly 10 provided herein can be used to measure the resolution of fundus imaging systems 12. Stated in another fashion, it is useful to quantitatively evaluate the performance degradation at a peripheral field of view of the fundus imaging system 12 due to optical aberrations from an optical assembly 22 of the fundus imaging system 12. The present system provides feedback to facilitate computational field aberration correction of information for subsequent images captured of one or both eyes 19 of the patient. As a result thereof, subsequent images of real patient eyes 19 will be more accurate. This will improve the quality of diagnosing and treating of patients in Ophthalmology. Further, subsequent images of real patient eyes 19 can be evaluated more accurately when the resolution of the fundus imaging system 12 at a plurality of spaced apart field locations is used to interpret these subsequent images.

The term "image" as used herein shall mean and include a two-dimensional image, or a two-dimensional array of data (information) that is captured and that can be used to generate the two-dimensional image.

The type of the fundus imaging system 12 analyzed with the assessment assembly 10 can be varied. A very simplified schematic illustration of a fundus imaging system 12 is illustrated in FIG. 1 for reference. In this embodiment, the fundus imaging system 12 can be a camera that includes a rigid system body 24 (illustrated as a box), an image sensor 26 (illustrated as a box), the optical assembly 22 (illustrated as a box), an illumination system 28 (illustrated as a box), and an imaging control system 29 (illustrated as a box). It should be noted that the typical fundus imaging system 12 will typically include many more components than illustrated in FIG. 1. For example, the fundus imaging system 12 can include a chin rest and/or forehead rest to facilitate the proper positioning of the patient human during evaluation.

The image sensor 24 can include a two dimensional array of sensors, with each sensor converting light to an electronic signal. The illumination system 28 can be used to selectively illuminate the artificial eye 14 or the eye of the patient.

The optical assembly 22 includes one or more lenses (not shown) that cooperate to form an image on the image sensor 24. The optical assembly 22 can have a curved imaging field. Unfortunately, the optical assembly 22 is not perfect (e.g. includes manufacturing defects). As provided herein, the assessment assembly 10 provided herein can be used to assess the imperfections of the optical assembly 22. Stated in another fashion, the assessment assembly 10 can be used to compute the field aberrations of the optical assembly 22.

The imaging control system 29 can control the components of the fundus imaging system 12. As a non-exclusive example, the imaging control system 29 can include one or more processors 29A (illustrated as a box), and one or more electronic storage devices 29B (illustrated as a box). In one embodiment, the imaging control system 29 collects and processes the information from the image sensor 24 to generate each image 20. As provided herein, the imaging control system 29 can utilize computational field aberration correction information obtained by the assessment assembly 10 to compensate for imperfections in the optical assembly 22, and generate more accurate subsequent images (not shown) of a patient's eye.

The artificial eye 14 is designed to simulate and mimic a real human eye 19. For example, the artificial eye 14 can be sized and shaped similar to a real eye 19 of a human. In FIG. 1, the artificial eye 14 is generally hollow sphere shaped, and includes an artificial cornea 30, an artificial pupil 32, an artificial lens 34, and an artificial retina region 36. In this embodiment, each of these components are sized, shaped and designed to simulate a real eye of a human. For example, the artificial retina region 36 is curved, concave, and is shaped like a portion of inner surface of a hollow sphere. The artificial retina region 36 forms a curved surface. As a non-exclusive example, the artificial eye 14 can have a diameter of between approximately twenty-one and twenty-seven millimeters.

As non-exclusive example(s), (i) the artificial cornea 30 can be made of a transparent material such as glass, polycarbonate, silicone as non-exclusive examples, (ii) the artificial pupil 32 can be made of an appropriate baffle material, (iii) the artificial lens 34 can be made of one or more lens or elements, and (iv) the artificial retina region 36 can be made of a silicon-based organic polymer, such as polydimethylsiloxane (PDMS). However, other materials can be utilized for one or more of these components.

In one, non-exclusive embodiment, a triplet glass lens can be used for the artificial lens 34 to mimic the lens 19C of the human eye 19. Alternatively, a plastic singlet or a lens group designed by sophisticated optical design can be used for the artificial lens 34 to better match the optical aberrations of the human eye 19.

In one embodiment, the curved, artificial retina region 36 is shaped and sized similar to the retina 19E of the human eye 19. Further, in certain embodiments, the artificial retina region 36 can be made of a material having scattering and depolarization properties that are similar to the scattering and depolarization properties of the human eye 19.

For example, the human eye 19 can have a degradation in degree of polarization of approximately 0.2 and the curved retina region 36 has a degradation in degree of polarization of approximately 0.8. In alternative, non-exclusive embodiments, the artificial eye 14 can be designed to have a depolarization power that is 0.15, 0.16, 0.17.0.18, 0.19, 0.2, 0.21, 0.22, 0.23, 0.24, or 0.25.

As used herein, the term depolarization power (DP) shall be equal to one minus the measured degree of polarization (DP=1-DOP). As alternative, non-exclusive examples, the curved retina region 36 has a depolarization power that is within 100, 99, 95, 90, 85, 80, 75, 70, 65 or 60 percent of a depolarization power of the retina 19E of the human eye 19. Further, as alternative, non-exclusive examples, the artificial cornea 30 and the artificial retina region 36 have a depolarization power that is within 100, 99, 95, 90, 85, 80, 75, 70, 65 or 60 percent of the depolarization power of the cornea 19A and the retina 19E of the human eye 19.

Scattering is one factor that causes depolarization. However, other factors, such as corneal and retinal birefringence also cause depolarization.

In one embodiment, the human eye 19 has a measured degree of polarization of approximately 0.83, and the retina 19E of the human eye 19 has a measured degree of polarization of approximately 0.25. As provided herein, in alternative, non-exclusive embodiments, the artificial eye 14 can be designed so that (i) the artificial cornea 30 and the artificial retina region 36 have a measured degree of polarization of 0.7, 0.71, 0.72, 0.73, 0.74, 0.75, 0.76, 0.77, 0.78, 0.79, 0.80, 0.81, 0.82, 0.83, 0.84, or 0.85; and/or (ii) the artificial retina region 36 have a measured degree of polarization of 0.2, 0.21, 0.22, 0.23, 0.24, 0.25, 0.26, 0.27, 0.28, 0.29, 0.3, 0.32, 0.34, 0.36, 0.38, 0.4.

In alternative, non-exclusive embodiments, the curved retina region has a degradation in degree of polarization that is within 100, 99, 95, 90, 85, 80, 75, 70, 65 or 60 percent of a degradation in degree of polarization of a retina of the human eye. For example, the curved retina region can be made of a polydimethylsiloxane and titanium dioxide mixture.

In one embodiment, the artificial retina region 36 is made of a polydimethylsiloxane and a scattering agent mixture that provide retinal scattering and depolarization properties that mimic the properties of the human eye 19. As an example, the artificial retina region 36 can be made of a polydimethylsiloxane and titanium dioxide (PDMS/TiO$_2$) mixture that provide retinal scattering and depolarization properties that mimic the properties of the human eye 19. Because the optical properties of the artificial retina region 36 are very close to those of the human retina, a more accurate evaluation of the fundus imaging system 12 is possible. Stated in another fashion, because the scattering and depolarization properties of the artificial eye 14 are close to those of the real human eye 19, a more accurate evaluation of the fundus imaging system 12 is possible.

In this embodiment, the polydimethylsiloxane (PDMS) is used as the substrate material, and titanium dioxide (TiO$_2$) as the scattering agent. Polydimethylsiloxane has great optical clarity ($\mu_s'$ and $\mu_a$=0 cm$^{-1}$), and has almost no scattering and absorption in the visible spectral band. As used herein, $\mu_s'$ is the scattering coefficient, and $\mu_a$ is the absorption coefficient. Further, polydimethylsiloxane has a comparable refractive index to human tissue (~1.4), it is optical stable over time, has physical durability, and the ability to form multilayer geometries. Titanium dioxide powder has a high scattering coefficient and low cost. When mixing titanium dioxide powder into polydimethylsiloxane at a specific ratio, the material with desired scattering property for making artificial retina region 36 is obtained.

Since $\mu_s'$ contributes to reflectance intensity much more than $\mu_a$, no absorbing agent is necessary. With this design, the retinal depolarization of the retina region 36 is mainly caused by scattering, which could change the polarization in a complicated way. Because the material of the retina region 36 has the scattering property of human retina 19E, its depolarization property should also be close to that of human retina 19E.

In one, non-exclusive embodiment, the polydimethylsiloxane and titanium dioxide mixture can have a ratio of 1.8 mg TiO$_2$ per 1 g PDMS to yield a $\mu_s'$ of ~5 cm$^{-1}$ at 630 nm which is comparable to human retinal tissue. In this embodiment, the ratio of PDMS to TiO$_2$ is 1 to 0.0018. It should be noted that the ratio of polydimethylsiloxane to titanium dioxide can be adjusted as necessary to achieve the desired scattering and depolarization properties of the artificial retina region 36. As alternative, non-exclusive examples, the ratio of PDMS to TiO$_2$ can be 1 to 0.0015, 1 to 0.0016, 1 to 0.0017, 1 to 0.0019, 1 to 0.0020, or 1 to 0.0021.

As provided herein, the problem of making the optical parameters of retina region 36 of the practice, artificial eye 14 close to those of the human retina 19E for accurately testing the fundus imaging system 12 is solved by using PDMS/TiO$_2$ mixture as the material for the retina region 36. Stated in another fashion, the use of PDMS/TiO$_2$ material for the artificial retina region 36 of the artificial eye 14 results in the artificial eye 14 yielding similar optical properties to the human retina 19E. Further, the artificial eye 14 mimics the properties of the human eye 19 without being filled with a viscous fluid.

As provided herein, the correct optical parameters of artificial retina region 36 is particularly important for testing the fundus imaging systems 12. For example, the realistic scattering and depolarization properties of the artificial retina region 36 are very important for testing fundus imaging systems 12 because they determine the intensity and optical properties of the retinal signal light received by the image sensor 26 and thus have significant impact on the quality of the images 20. A practice eye with wrong optical properties of retina cannot accurately reflect the imaging performance of a fundus imaging device.

The type of manufacturing process used to make the components of the artificial eye 14 can be varied. As non-exclusive examples, a molding process or three-dimensional printing can be used to make one or more of the components.

The resolution chart assembly 16 includes one or more curved, flexible, resolution test charts 40 that are fixedly coupled to the retina region 36. With this design, each resolution test chart 40 is flexible to curved to follow a portion of the curve of the retina region 36.

The spacing and number of resolution test charts 40 can be varied. As alternative, non-exclusive examples, the resolution chart assembly 16 can include 1, 2, 3, 4, 5, 6, 7, 8, 9, 10, 11, 12, 13, 14, 15, or 20 resolution test charts 40. With this design, multiple resolution test charts 40 can be attached to different sites of the retina region 36 to assess resolutions throughout the full field of view of the fundus imaging system 12. The resolution chart assembly 16 is discussed in more detail below.

The analysis system 18 compares the information from the images 20 (captured of the artificial eye 14 and the resolution chart assembly 16) to the known resolution test charts 40, and determines the optical resolution of the fundus imaging system 12. With this design, the analysis system 18 can quantitatively evaluate the performance degradation at a peripheral field of view of the fundus imaging system 12 due to optical aberrations from the optical assembly 22. Stated in another fashion, with the present design, the analysis system 18 can review one or more images and provide a quantitative resolution measurement of the fundus imaging system at a plurality of spaced apart field locations.

With the present design, in certain embodiments, the analysis system 18 can measure the resolution performance at many points in the field of view for the fundus imaging system 12. As a result thereof, the analysis system 18 can determine the performance of the fundus imaging system 12.

As a non-exclusive example, the analysis system 18 can include one or more processors 18A (illustrated as a box), and one or more electronic storage devices 18B (illustrated as a box) for processing the information from the images 20 and the information regarding the known resolution test charts 40.

Figure 2:
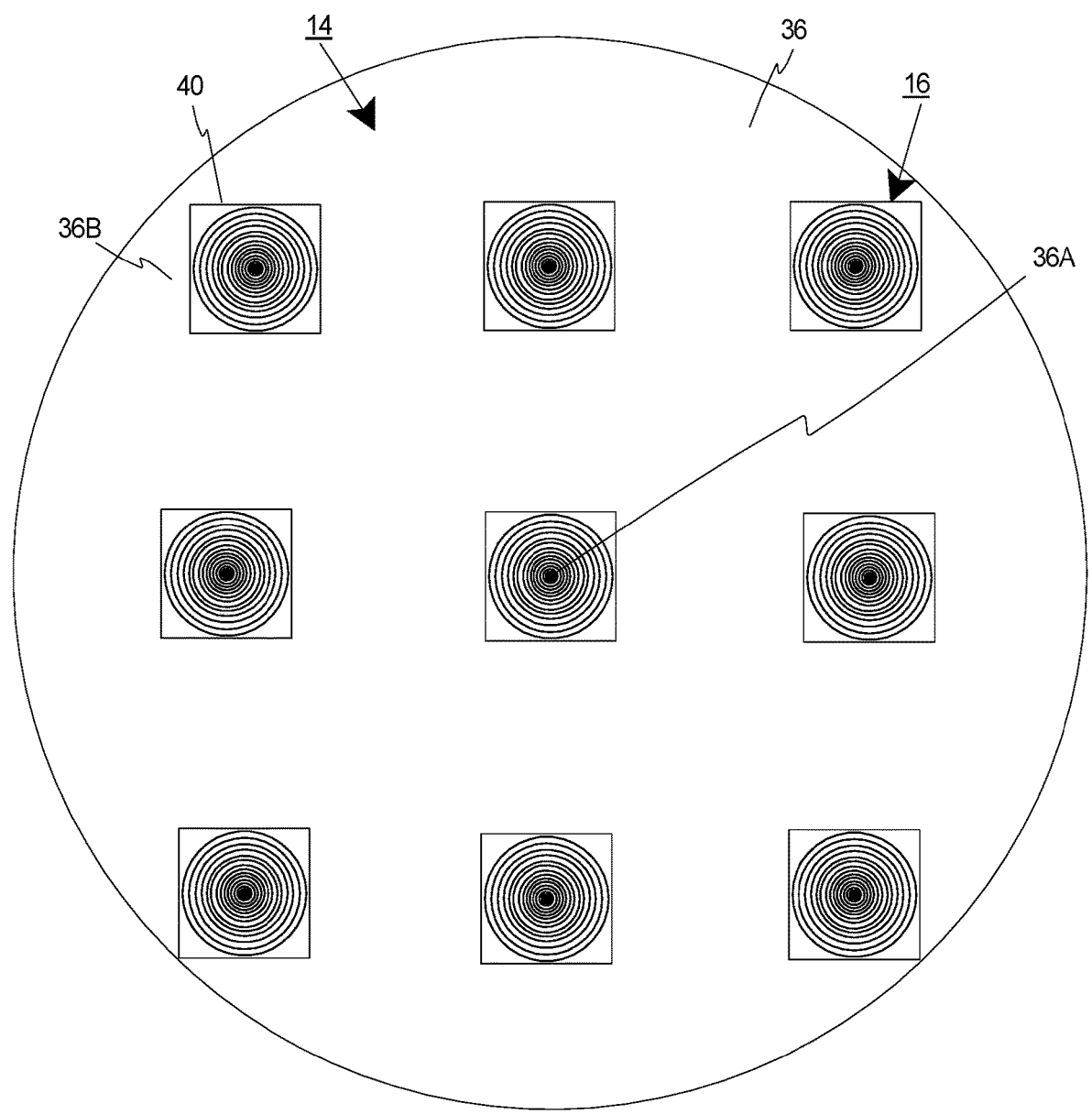
FIG. 2 is a simplified front view of a portion of an artificial eye and a resolution chart assembly having features of the present invention.

FIG. 2 is a simplified front view of the curved retina region 36 of the artificial eye 14, and one, non-exclusive embodiment of the resolution chart assembly 16. In this embodiment, the resolution chart assembly 16 includes nine, curved resolution test charts 40 that are spaced apart and that are secured to the curved retina region 36 at different locations. Further, in this embodiment, each resolution test chart 40 is small, flexible, curved and has the shape of a segment of a hollow sphere. Alternatively, the resolution chart assembly 16 can include more than nine or fewer than nine resolution test charts 40.

In FIG. 2, the nine resolution test charts 40 are organized in a three by three rectangular shaped grid. Alternatively, the resolution test charts 40 can be organized in another fashion. In this simplified example, one of the resolution test charts 40 is positioned at the center (e.g. central part) 36A of the retina region 36. However, resolution test charts 40 can be positioned at locations other than the center of the retina region 36. For example, one or more resolution test charts 40 can be positioned at a peripheral part 36B of the retina region 36.

The space between adjacent resolution test charts 40 can be varied. For example, the test charts 40 can be spaced apart and positioned based on the desired field points being evaluated.

By virtue of its small size, multiple resolution test charts 40 are attached to different sites of the artificial retina region 36, enabling a full assessment of resolution at the center field of view as well as the peripheral, and a plurality of locations therebetween. The difference in resolution between the center and peripheral field of view can also quantitatively reveal the degradation of imaging performance in peripheral areas due to optical aberrations of the optical assembly 22 (illustrated in FIG. 1).

The material utilized for each resolution test chart 40 can be varied. In one non-exclusive embodiment, each resolution test chart 40 is flexible, and can be made of a silicon-based organic polymer, such as polydimethylsiloxane (PDMS). However, other flexible materials can be utilized. In another example, each resolution test chart 40 can be made of a mixture of PDMS and titanium dioxide ($TiO_2$) power.

In one embodiment, prior to attachment, each resolution test chart 40 is generally planar, rectangular shaped, and flexible. Subsequently, when each resolution test chart 40 is secured to the retina region 36, it can flex to conform to the curved retina region 36. Stated in another fashion, although each resolution test chart 40 is substantially planar, it is very small, thin, and soft. Thus, multiple resolution test charts 40 can be easily attached to and conform to the curved artificial retina region 36.

The method used to attach each resolution test chart 40 to the artificial retina region 36 can also vary. In one non-exclusive embodiment, if each resolution test chart 40 and the artificial retina region 36 are made of PDMS or a PDMS/$TiO_2$ mixture, each resolution test chart 40 can be irreversibly bonded to the artificial retina region 36 through a surface treatment of air (oxygen) plasma. Alternatively, an adhesive or other method can be used to fixedly secure each resolution test chart 40 to the artificial retina region 36. Still alternatively, each resolution test chart 40 can be reversibly bonded to the artificial retina region 36.

Figure 3A:
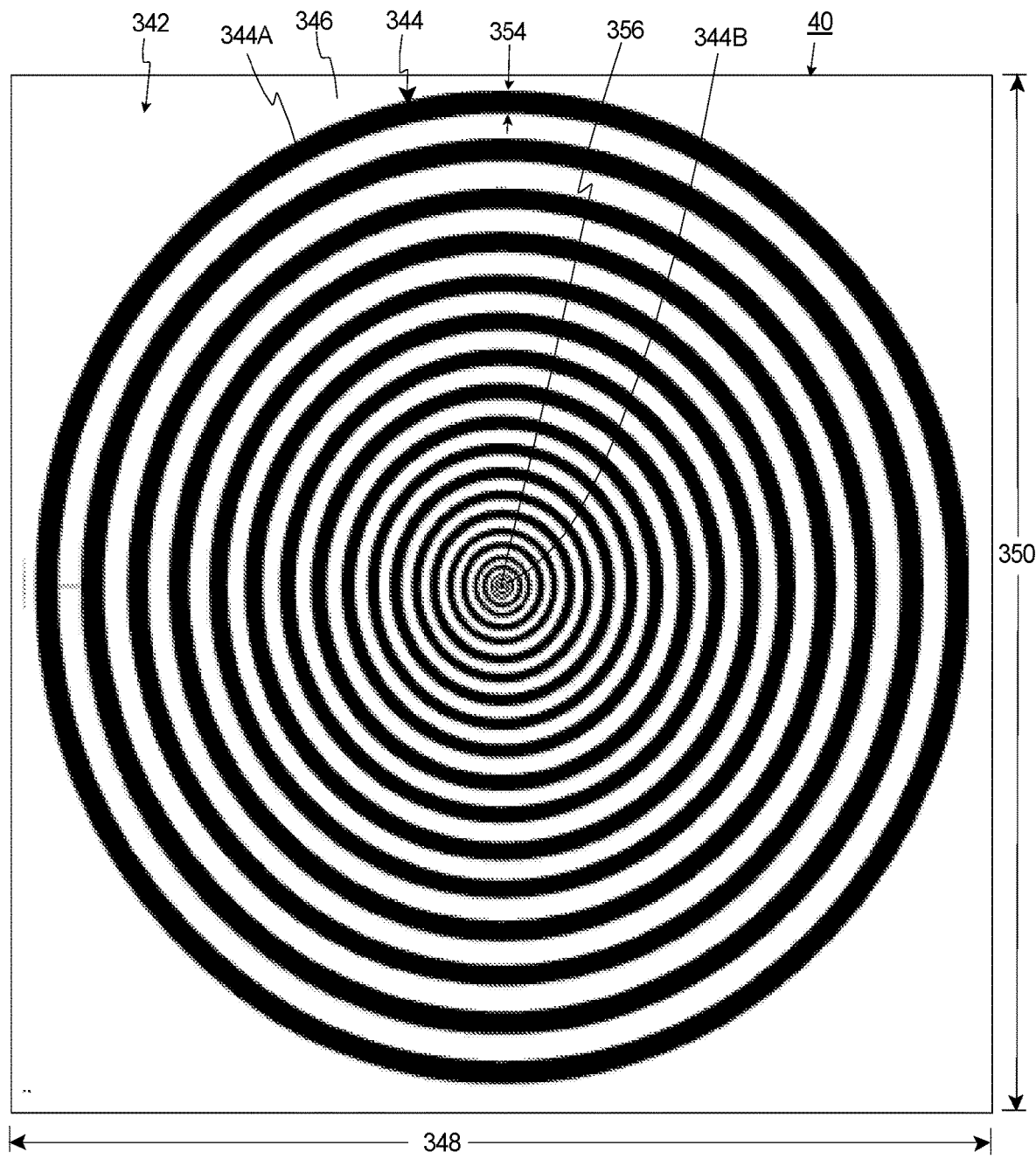
FIG. 3A is a simplified front view of a resolution test chart having features of the present invention.
Figure 3B:
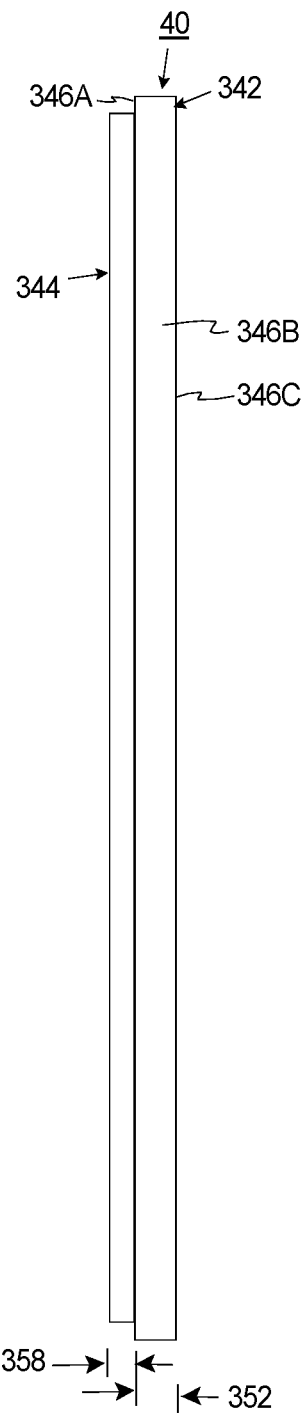
FIG. 3B is a simplified, side view of the resolution test chart of FIG. 3A.
Figure 3C:
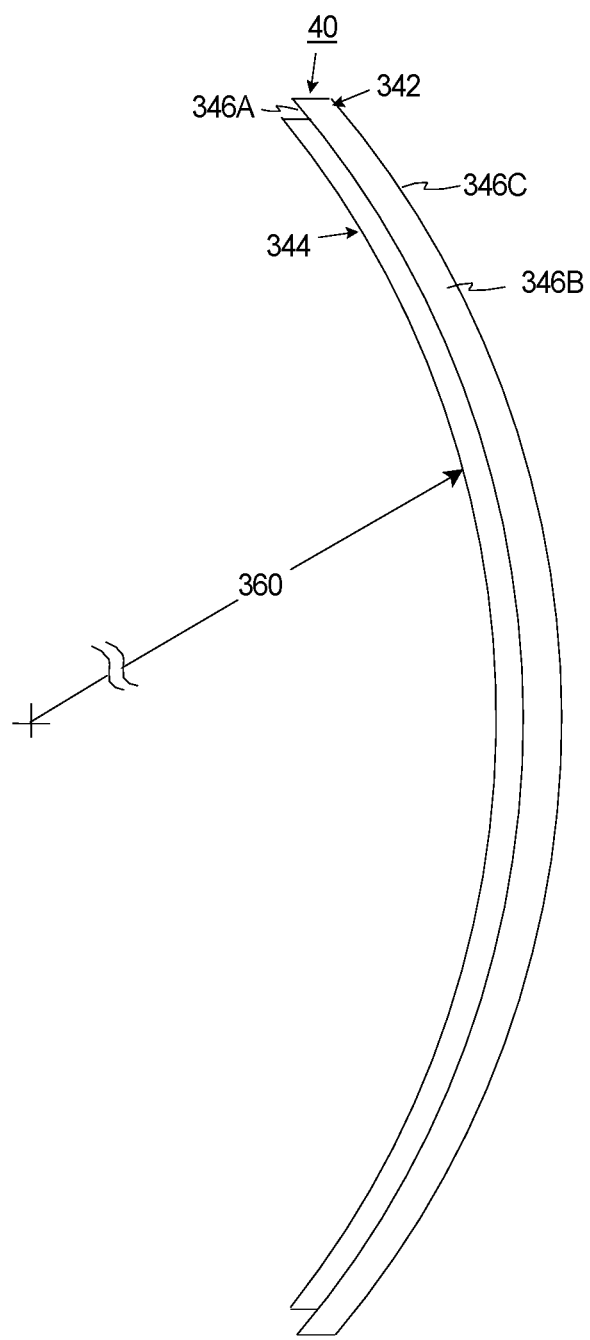
FIG. 3C is a simplified, side, cut-away view of the resolution test chart of FIG. 3A in a curved configuration.

FIG. 3A is a simplified front view of one of the resolution test charts 40 of FIG. 2, prior to attachment to the retina region 36 (illustrated in FIG. 2). FIG. 3B is a simplified, side view of the resolution test chart 40 of FIG. 3A prior to attachment. Further, FIG. 3C is a simplified, side, cut-away view of the resolution test chart 40 of FIG. 3A in a curved configuration after attachment to the retina region (not shown in FIG. 3C). It should be noted that the other resolution test charts 40 of FIG. 2 can be similar or slightly different than the design illustrated in FIGS. 3A-3C.

As provided above, prior to attachment and as illustrated in FIGS. 3A and 3B, the resolution test chart 40 can be generally planar, rectangular shaped. In one embodiment, the resolution test chart 40 includes a chart body 342 and a plurality of space apart chart features 344.

The design of the chart body 342 can be varied. In FIGS. 3A and 3B, prior to attachment, the chart body 342 is generally planar square shaped, and has a front surface 346A, four sides 346B, and a back surface 346C that is secured to the artificial eye 14 (illustrated in FIG. 1). As alternative, non-exclusive examples, the chart body 342 (prior to attachment) can have (i) a width 348 of approximately 0.5, 0.75, 1, 1.25, or 1.5 millimeters; (ii) a length 350 of approximately 0.5, 0.75, 1, 1.25, or 1.5 millimeters; and (iii) a thickness 352 of approximately 20, 30, 40, 50, 60, 70, 80 or 100 microns. In one particular example, the chart body 342 is square and has a width 348 of one millimeter, a length 350 of one millimeter, and a thickness 352 of fifty microns. In alternative, non-exclusive examples, the front surface 346A has a chart surface area of less than 0.5, 0.75, 1, 5, 10, 20, 25, 30, 40 or 50 millimeters squared. However, other shapes, sizes, and configurations are possible.

The shape, size, spacing, and/or number of chart features 344 can be varied. In the embodiment illustrated in FIGS. 3A-3C, each of the chart features 344 is a circular ring that extends away (raised) from the chart body 342. Moreover, in this non-exclusive embodiment, the ring shaped chart features 344 are substantially concentric. More specifically, as illustrated in FIG. 3A, the test chart 40 includes twenty concentric, raised ring shaped, chart features 344. Alternatively, the test chart 40 can include 10, 11, 12, 13, 14, 15, 16, 17, 18, 19, 21, 22, 23, 24, 25, 26, 27, 28, 29 or 30 chart features 344. However, a greater number or fewer number of chart features 344 can be utilized. Further, other shapes of the chart features 344, or other configurations of the chart features 344 can be utilized.

Moreover, in FIG. 3A, each of the concentric chart features 344 will have a different diameter and a different feature width 354. More specifically, in one embodiment, moving radially outward from a center 356 of the chart body 342, each subsequent chart feature 344 will have a larger diameter and a larger feature width 354. Stated in another fashion, (i) an outermost feature 344A will have the largest diameter and the largest feature width 354, (ii) the innermost feature 344B will have the smallest diameter and the smallest feature width 354, and (iii) each subsequent feature 344 moving outward from the center 350 will have a slightly larger diameter and a slightly larger feature width 354. In one non-exclusive embodiment, the diameter of the chart features 344 varies from approximately 0 to 7 millimeters, and the feature width 354 of the chart features 344 varies from one to forty microns. However, other ranges can be used to achieve other resolutions.

Further, a height 358 of each raised chart feature 344 can also be varied. As alternative, non-exclusive examples, the height 358 of each raised chart feature 344 can be approximately 20, 30, 40, 50, 60, 70, 80 or 100 microns.

With the present design, the optical properties of each of the resolution test charts 40 is close to those of real human retina, providing reasonable signal strength and thus true assessment of imaging performance of the fundus image system 12 (illustrated in FIG. 1). It should be noted that the design of one or more of the resolution test charts 40 can be different than that illustrated in FIGS. 3A-3C.

It should also be noted that the design of one or more of the chart features 344 can be different than that illustrated in FIGS. 3A-3C. For example, the shape of one or more of the chart features 344 can be linear, arched, rectangular, triangular, or octagonal. As a specific example, the test chart 40 can include a plurality of spaced apart, parallel lines with different feature widths. Generally, the most important characteristic of a resolution test chart is that it has to have at least two features of a same width (spacing is also equal to the width) so that the resolution of the imaging system can be determined by the evaluation of the pair.

Moreover, the resolution test chart 40 is flexible (not very stiff) so that the resolution test chart 40 can easily conform to the shape of the curved retina region 36. As alternative, non-exclusive examples, the resolution test chart 40 has an elasticity of less than 0.6, 0.8, 1, or 1.2 mega pascal.

It should be noted that the amount of curve of the resolution test chart 40 when it is secured to the curved retina region 36 will vary according to the shape of the retina region 36. Stated in another fashion, each resolution test chart 40 will curve to conform to the shape of the retina. For example, in alternative, non-exclusive examples, the resolution test chart 40 will have a radius of curvature 360 of at least 8, 10, 12, or 14 millimeters when it is secured to the curved retina region 36.

As provided herein, one or more resolution test charts 40 can have a plurality of spaced apart chart features 344, with at least two of the chart features 344 having a different feature width. In one embodiment, each chart feature 344 has a ring shape. Further, the chart features 344 can be substantially concentric.

In certain embodiments, one or more of the resolution test charts 40 have the same chart features 344. Alternatively, one or more of the resolution test charts 40 can have a different design.

Figure 4:
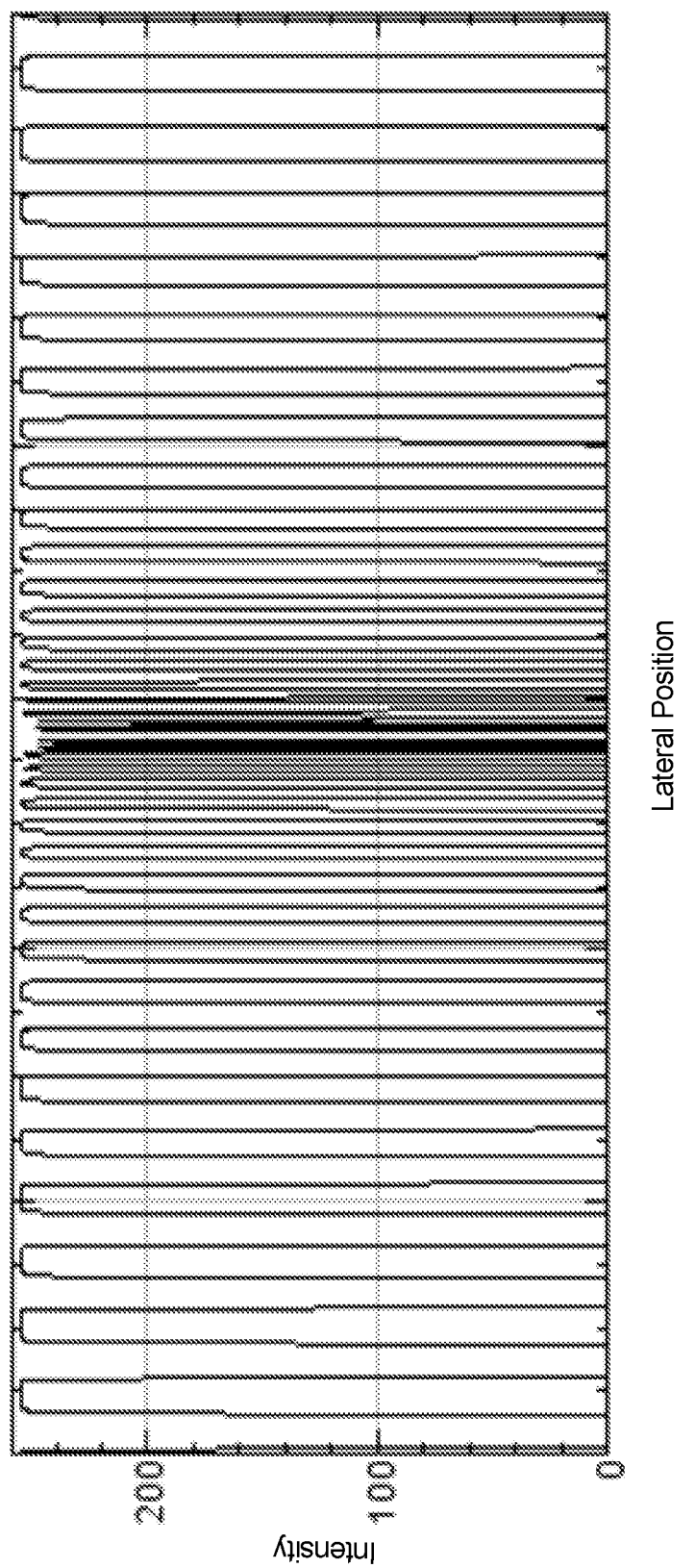
FIG. 4 is a graph that illustrates an intensity distribution versus lateral position of the chart features of the resolution test chart of FIG. 3.

FIG. 4 is a graph that illustrates an intensity distribution versus lateral position for the chart features 344 of the resolution test chart 40 illustrated in FIG. 3A as you move from left to right through the center 356 of the resolution test chart 40. In one non-exclusive embodiment, to measure the resolution of an imaging system, an image of the resolution chart is first captured with the imaging system. Next, a line across the center of the chart features in the image is drawn. Subsequently, an intensity distribution along the line can be plotted. If the smallest ring pair that can be resolved are of a three micron width (their spacing is equal to their width), the imaging system resolution is three microns. In this non-exclusive example, resolution is measured by finding out the smallest resolvable ring pair. It should be noted, in this example, when the line to plot intensity distribution is drawn, it must be across the feature center. If not, the widths of rings are not correctly displayed on the plot, and thus the measurement would be less accurate.

Figure 5:
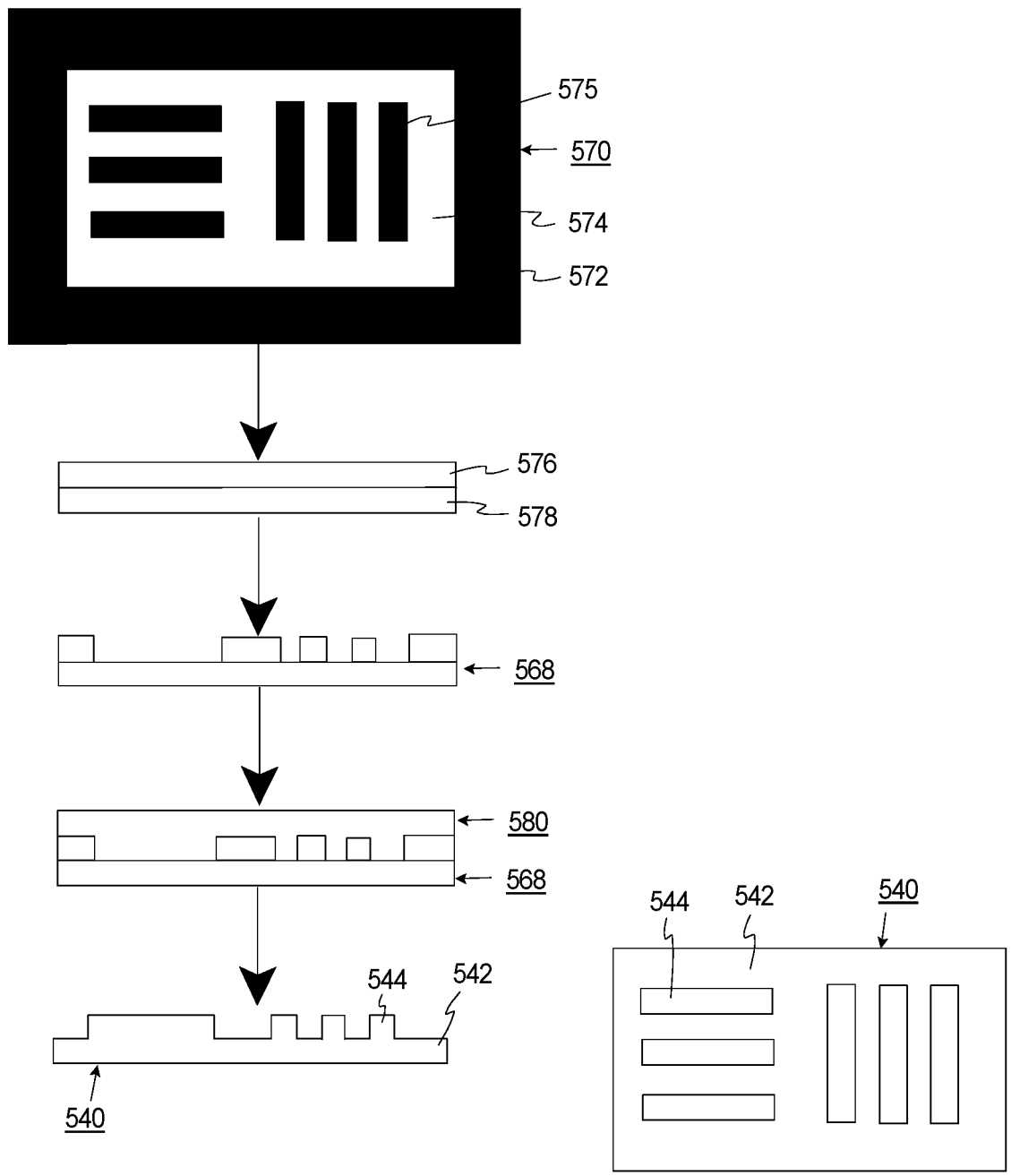
FIG. 5 is a simplified illustration of another embodiment of the resolution test chart, and how the resolution test chart can be fabricated.

FIG. 5 is a simplified illustration of another embodiment of the resolution test chart 540, and how the resolution test chart 540 can be fabricated. In FIG. 5, both a side view and a top view of the resolution test chart 540 is illustrated prior to attachment to the retina region (not shown). In the simplified embodiment illustrated in FIG. 5, the resolution test chart 540 includes a rectangular-shaped chart body 542, and six linear chart features 544 that extend above the chart body 542. In FIG. 5, the chart features 544 are organized as two sets of three, spaced apart parallel lines, with the sets being transverse to each other.

The method used to manufacture the test chart 540 can be varied. In one embodiment, the approach and procedure to fabricate the resolution test chart 540 can use photolithography to first make a mold 568, and subsequently use soft lithography (e.g. the mold 568) to form the test chart 540.

In FIG. 5, a monochrome photomask 570 can first be made that includes opaque regions 572 (illustrated in black) and transparent regions 574 (illustrated in white) that will define the shape of the chart features 544. In FIG. 5, the photomask 570 includes a two dimensional layout of the desired pattern 575 of resolution features (straight lines with desired feature widths) that can be commercially printed with very high resolution.

Next a photoresist 576 on a silicon wafer 578 is provided. Subsequently, the photomask 570 is illuminated with an energy beam (not shown) (e.g. an ultraviolet light) and the pattern from the photomask 570 is transferred to the photoresist 576 to create the mold 568 on the wafer 578. In one embodiment, the mold 568 is produced by patterning SU8 epoxy-based photoresist 576 on a silicon substrate 578 using standard photolithography techniques. The pattern of the chart features appear as deep grooves (e.g. 50 micron) on the mold 568.

Next, a material 580 (e.g. the PDMS+$TiO_2$) is used to fill the mold 568 to form the resolution test chart 540. For example, a mixture of 1.8 mg of $TiO_2$ per gram of PDMS can be used to make a soft replica against the silicon mold 568. The PDMS/$TiO_2$ mixture can be used as tissue imaging phantom as its optical scattering property is similar the scattering property of human tissue. In this example, fabrication of the test chart 540 can be performed by reverse replica by soft lithography. More specifically, the mold 568 can be spin-coated with the PDMS/$TiO_2$ mixture at a certain spin rate so that the reverse replica will have a 50 micron thickness the chart body 542 (determined by the spin rate) and 50 µm height chart features 544 (formed by the grooves on the mold).

Finally, after curing of the material, the resolution test chart 540 can be removed from the mold 568. For example, it can be trimmed to a one millimeter by one millimeter piece and attached to the artificial retina (not shown in FIG. 5).

Figure 6:
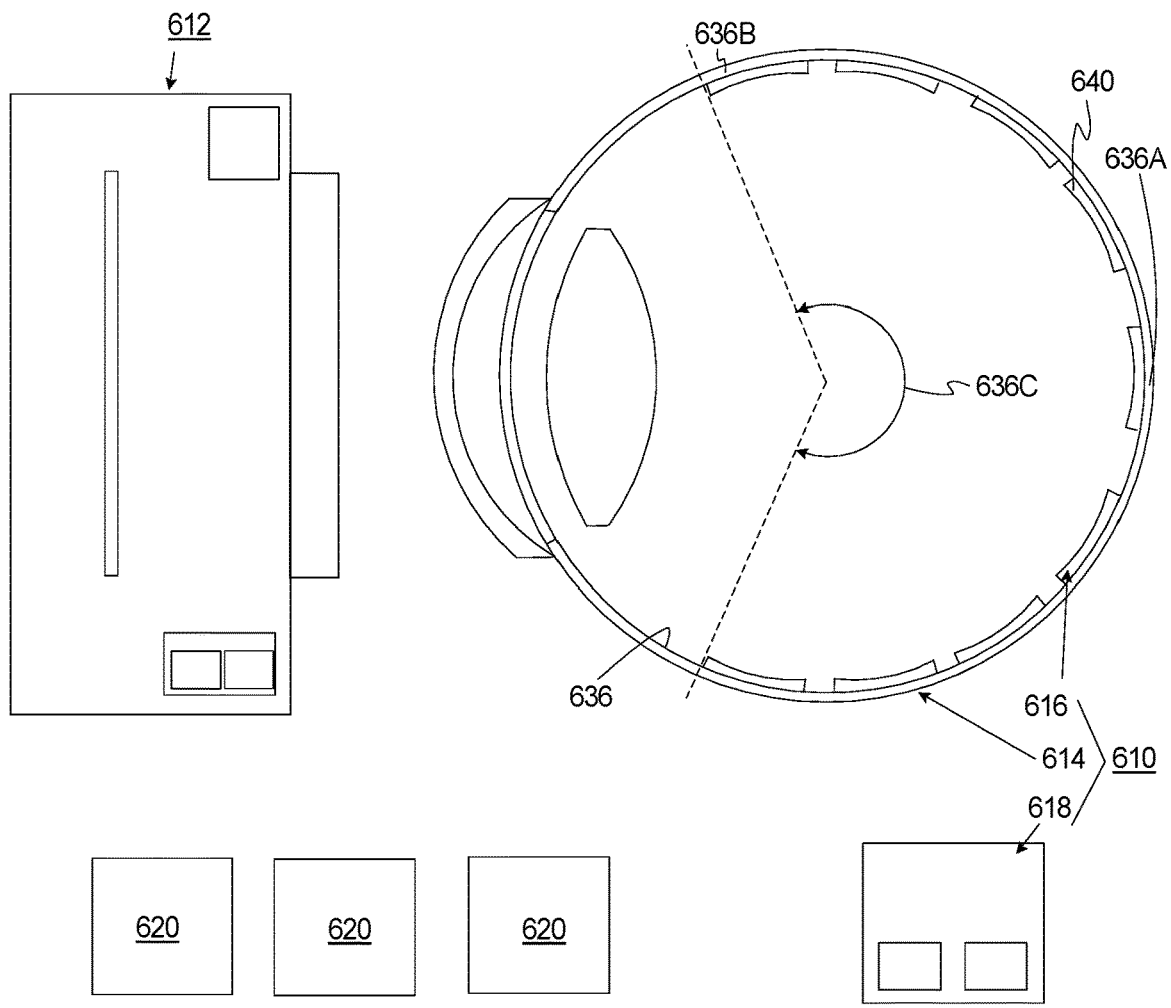
FIG. 6 is a simplified illustration of a human eye, a fundus imaging system and another implementation of an assessment assembly having features of the present invention.
Figure 6:
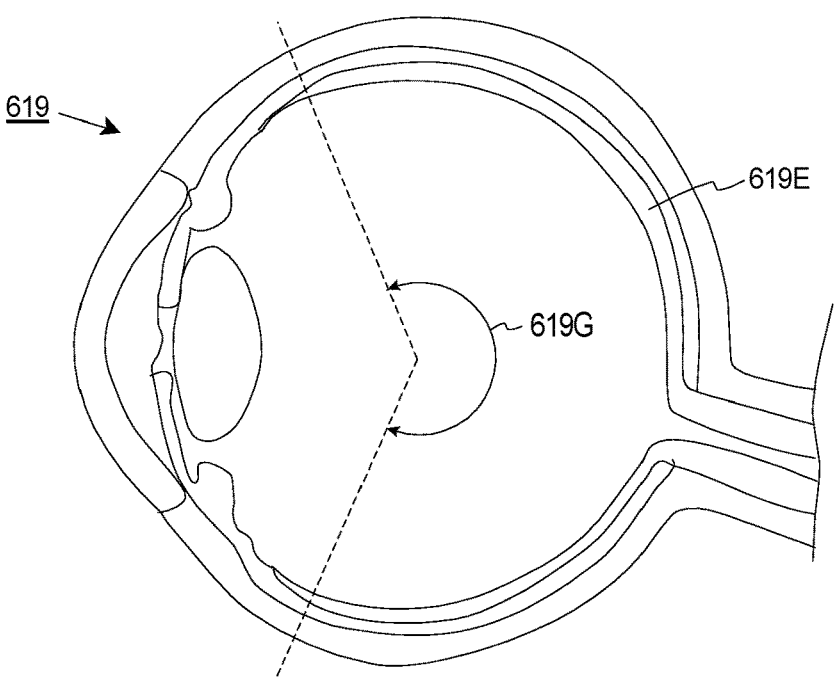

FIG. 6 is a simplified illustration of a human eye 619, and another implementation of the assessment assembly 610 for a fundus imaging system 612 that includes an artificial eye 614, a resolution chart assembly 616 fixedly coupled to the artificial eye 614, and an analysis system 618. In this embodiment, the artificial eye 614, and the analysis system 618 are similar to the corresponding components described above and illustrated in FIG. 1. However, the fundus imaging system 612 and the resolution chart assembly 616 are slightly different.

FIG. 6 also includes the simplified illustration of a human eye 619 that is similar to the human eye 19 described above and illustrated in FIG. 1. However, in FIG. 6, an ultra-widefield region 619G of the retina 619E is labeled. In certain embodiments, the ultra-widefield retina region 619G includes approximately two hundred degrees (~200°) field area of the retina 619E.

The fundus imaging system 612 can be similar to the corresponding described above and illustrated in FIG. 1. However, in the embodiment of FIG. 6, the fundus imaging system 612 is also able to capture one or more ultra-widefield images 620. As a result thereof, the fundus imaging system 612 can be used to analyze ultra-widefield regions 619G of the human eye 619, e.g. approximately two hundred degrees (~200°) field area of the retina 619E. With this design, the fundus imaging system 612 can be used to analyze larger portions of the human eye 619 to better test the human eye 619.

With the present design, the fundus imaging system 612 can be controlled to capture one or more ultra-widefield images 620 of the artificial eye 614 and the resolution chart assembly 616. Subsequently, information from one or more of the images 620 can be analyzed (e.g. by the analysis system 618) to evaluate the optical resolution of the fundus imaging system 612 at a number of spaced apart field locations in the field of view of the fundus imaging system 612.

The present system provides feedback to facilitate computational field aberration correction of information for subsequent images captured of one or both eyes 619 of the patient. As a result thereof, subsequent images of real patient eyes 619 will be more accurate. This will improve the quality of diagnosing and treating of patients in Ophthalmology.

The resolution chart assembly 616 again includes one or more curved, flexible, resolution test charts 640 that are fixedly coupled to the retina region 636. With this design, each resolution test chart 640 is curved to follow a portion of the curve of the retina region 636. In this embodiment, the curved retina region 636 includes a central part 636A, and a peripheral part 636B. In this embodiment, the peripheral part 636B includes an ultra-widefield portion 636C of the curved retina region 636.

As provided herein, the resolution chart assembly 616 can include one or more resolution test charts 640 that are positioned in (coupled to) the central part 636A and the peripheral part 636B (including the ultra-widefield region 636C) of the retina region 636 of the artificial eye 614. In certain embodiments, the ultra-widefield retina region 636C includes approximately two hundred degrees (~200°) field area of the retina region 636 of the artificial eye 614.

The number of resolution test charts 640 in the ultra-widefield region 636C can be varied. For example, the resolution chart assembly 616 can include a plurality of resolution test charts 640 distributed around the ultra-widefield retina region 636C. As alternative, non-exclusive examples, the resolution chart assembly 616 can include 1, 2, 3, 4, 5, 6, 7, 8, 9, or 10 resolution test charts 640 in the ultra-widefield retina region 636C, with other resolution test charts 640 being positioned in different areas of the retina region 636. With this design, multiple resolution test charts 640 can be attached to different sites of the retina region 636 to assess resolutions throughout the full field of view of the fundus imaging system 612.

In this embodiment, each resolution test charts 640 can be similar to the corresponding component described above.

The analysis system 618 compares the information from the images 620 (captured of the artificial eye 614 and the resolution chart assembly 616) to the known resolution test charts 640, and determines the optical resolution of the fundus imaging system 612. With this design, the analysis system 618 can quantitatively evaluate the performance degradation at a peripheral field of view of the fundus imaging system 612 due to optical aberrations.

It is understood that although a number of different embodiments of the resolution test chart have been illustrated and described herein, one or more features of any one embodiment can be combined with one or more features of one or more of the other embodiments, provided that such combination satisfies the intent of the present invention.

While a number of exemplary aspects and embodiments of the resolution test chart have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. An assessment assembly for assessing a fundus imaging system, the assessment assembly comprising: a curved surface; at least one, flexible, resolution test chart that is formed to include at least one chart feature, and that is subsequently attached onto the curved surface, wherein the curved surface is a curved retina region of an artificial eye, and the at least one resolution test chart is attached onto the curved retina region; and wherein the artificial eye is shaped similar to a real eye of a human; and an analysis system that analyzes information from at least one image captured of the at least one resolution test chart that is attached onto the curved surface by the fundus imaging system to assess a resolution of the fundus imaging system.

2. The assessment assembly of claim 1 wherein the curved retina region has scattering and depolarization properties that are similar to the scattering and depolarization properties of a human eye.

3. The assessment assembly of claim 1 wherein the at least one resolution test chart is coupled to an ultra-widefield portion of the retina region of the artificial eye.

4. The assessment assembly of claim 1 further comprising a fundus imaging system that captures at least one image of the at least one, flexible, resolution test chart.

5. The assessment assembly of claim 1 wherein each of the at least one resolution test chart has an elasticity of less than 1.2 mega pascal.

6. The assessment assembly of claim 1 wherein each of the at least one resolution test chart has a chart surface area of less than fifty millimeters squared.

7. The assessment assembly of claim 1 wherein each of the at least one resolution test chart has a plurality of spaced apart chart features, wherein at least two of the chart features have a different feature width.

8. The assessment assembly of claim 7 wherein for each of the at least one resolution test chart, each chart feature has a ring shape.

9. The assessment assembly of claim 8 wherein for each of the at least one resolution test chart, the chart features are substantially concentric.

10. The assessment assembly of claim 1 further comprising at least two resolution test charts that are spaced apart.

11. The assessment assembly of claim 1 further comprising at least two resolution test charts with the same chart features, wherein one resolution test chart is attached onto a central part of the curved surface, and the other resolution chart is attached onto peripheral part of the curved surface.

12. A method for assessing a fundus imaging system, the method comprising: providing an artificial eye that includes a curved retina region; attaching at least one, flexible, resolution test chart to the curved retina region of the artificial eye, the at least one, flexible, resolution test chart being formed to include at least one chart feature before subsequently being attached to the curved retina region of the artificial eye; capturing at least one image of the curved retina region including the at least one resolution test chart with the fundus imaging system; and assessing a resolution of the fundus imaging system by analyzing the image.

13. The method of claim 12 wherein the step of providing includes the artificial eye being shaped similar to a real eye of a human; and wherein the step of attaching includes attaching the at least one resolution test chart to an ultra-widefield portion of the retina region of the artificial eye.

14. An artificial eye that mimics a human eye, comprising: a curved, artificial retina region wherein at least one flexible resolution test chart is selectively and fixedly coupled to the curved retina region, wherein the at least one resolution test chart is formed to include a chart body and at least one chart feature before the at least one resolution test chart is subsequently selectively and fixedly coupled to the curved retina region.

15. The artificial eye of claim 14 wherein the artificial retina region has scattering and depolarization properties that are similar to the scattering and depolarization properties of the human eye.

16. The artificial eye of claim 14 wherein the at least one resolution test chart is coupled to an ultra-widefield portion of the retina region of the artificial eye; and wherein the artificial eye is shaped similar to a real eye of a human.

17. The artificial eye of claim 14 wherein the curved retina region has a depolarization power that is within sixty percent of a depolarization power of a retina of the human eye.

18. The artificial eye of claim 14 wherein the curved retina region is made of a polydimethylsiloxane and titanium dioxide mixture.

19. A fundus imaging system comprising: the artificial eye of claim 14; an imaging unit that may capture at least one image of the at least one flexible resolution test chart that is attached onto the artificial retina region of the artificial eye; and an analysis system that analyzes information from the at least one image captured of the at least one resolution test chart by comparing to information from images of known resolution test charts to assess a resolution of the fundus imaging system.

20. The assessment assembly of claim 1 wherein the chart body of the at least one resolution test chart is substantially planar prior to being attached to the curved surface.

* * * * *